United States Patent

Morita et al.

[11] 4,163,864
[45] Aug. 7, 1979

[54] PROCESS FOR PREPARING 2-METHYL-3-PRENYL-4,5,6-TRIMETHOXY-PHENOL

[75] Inventors: Eiichi Morita; Hirosaburo Ejiri, both of Saitama; Keizo Takayanagi, Isezaki; Yukio Morita; Yasuhide Tanaka, both of Saitama; Shizumasa Kijima, Tokyo; Kimio Hamamura, Chiba; Isao Yamatsu, Saitama, all of Japan

[73] Assignee: Eisai Co., Ltd., Tokyo, Japan

[21] Appl. No.: 878,470

[22] Filed: Feb. 16, 1978

[30] Foreign Application Priority Data

Mar. 7, 1977 [JP] Japan .................................. 52-23901

[51] Int. Cl.² .............................................. C07C 41/00
[52] U.S. Cl. ..................................... 568/628; 568/651
[58] Field of Search ................... 260/613 D; 568/628, 568/651

[56] References Cited

U.S. PATENT DOCUMENTS

| | | | |
|---|---|---|---|
| 3,349,113 | 10/1967 | Gloor et al. | 260/613 D X |
| 4,039,573 | 8/1977 | Kijima et al. | 260/613 D X |
| 4,061,660 | 12/1977 | Kijima et al. | 260/613 D X |
| 4,062,879 | 12/1977 | Kijima et al. | 260/613 D X |

Primary Examiner—Bernard Helfin

Attorney, Agent, or Firm—Blanchard, Flynn, Thiel, Boutell & Tanis

[57] ABSTRACT

2-methyl-3-prenyl-4,5,6-trimethoxyphenol of the formula:

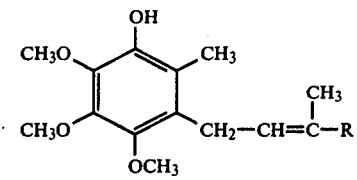

wherein R represents a group of the formula:

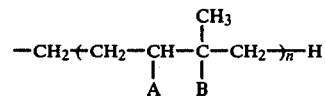

wherein n is an integer of 0 to 9 and A and B represent hydrogen atom or A—B may form a bond, is prepared by reacting 6-methyl-2,3,4-trimethoxyphenol with a prenol or isoprenol substituted by the group R as defined above in the presence of a complex catalyst comprising Lewis acid and a silica-alumina compound.

2 Claims, No Drawings

PROCESS FOR PREPARING 2-METHYL-3-PRENYL-4,5,6-TRIMETHOXYPHENOL

BACKGROUND OF THE INVENTION

1. Field of the Invention

The present invention relates to a process of the preparation of 2-methyl-3-prenyl-4,5,6-trimethoxyphenol of general formula (I):

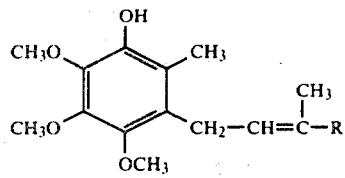

wherein R represents a group of the formula:

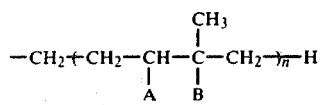

n being an integer of 0-9, and A and B represent hydrogen atom or A—B may form a bond. Compound (I) is a useful intermediate of 2,3-dimethoxy-5-methyl-6-prenyl-1,4-benzoquinone of general formula (II):

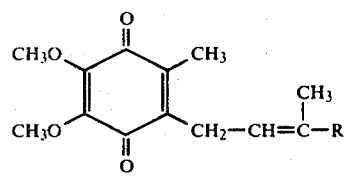

wherein R has the same meaning as above.

Compound (II) is known as coenzyme Q. Particularly, 2,3-dimethoxy-5-decaprenyl-6-methyl-1,4-benzoquinone of the formula wherein A and B together form a bond and n is 9 [2,3-dimethoxy-5-(3,7,11,15,19,23,27,31,35,39-decamethyltetracontadec-aene-2,6,10,14,18,22,26,30,34,38-yl)-6-methyl-1,4-benzoquinone] called "coenzyme $Q_{10}$" takes part in electron transport system in vivo and it also plays a very important role in energy generation. Coenzyme $Q_{10}$ improves disorder in the myocardium tissue due to ischemia, increases cardiac minute volume which has once decreased and exhibits antagonism against Na retention of aldosterone. Coenzyme $Q_{10}$ is thus effective for the prevention and treatment of congestive cardiac insufficiency, congestion of the lung, swelling of the liver and angina pectoris.

DESCRIPTION OF PRIOR ARTS

As processes for the synthesis of compound (II), there have been known processes wherein 2,3-dimethoxy-t-methyl-1,4-benzohydroquinone or a 1-monoacyl derivative thereof is reacted with (iso)-prenol or a reactive derivative thereof in the presence of a catalyst comprising a proton acid such as formic acid, sulfuric acid, hydrochloric acid, phosphoric acid or p-toluenesulfonic acid; a Lewis acid such as zinc chloride, aluminum chloride, boron trifluoride or an ether complex thereof; or a mixture of them to obtain a corresponding hydroquinone compound (see Japanese Patent Publications Nos. 17513/1964 and 3967/1971) and then the reaction product is further reacted with an oxidizing agent to obtain a corresponding benzoquinone compound (see Japanese Patent Publication No. 17514/1964).

However, according to those processes, the yield of the intended quinone compound is very poor, namely, the yield of even the crude product is up to 30%, since the yield in the condensation step is poor and, therefore, there is room for improvement. Further, the catalysts used have strong corrosive properties which are unsuitable for the devices used and, in addition, metals thus eluted contaminate the product. This disadvantage is inevitable when those processes are carried out on a commercial basis.

Those processes have many industrial demerits, namely, that if said catalyst is used, a neutralization step and an extraction step are required in the separation of the intended product from the reaction products and that a large amount of catalyst is used as compared with the starting materials which catalyst must be discarded after the reaction in many cases. Thus, the processes are not preferred from the viewpoints of cost and environmental pollution.

SUMMARY OF THE INVENTION

After investigations for the purpose of developing a process for obtaining quinone compounds (II) efficiently, the inventors have recognized that said demerits can be overcome and the object can be attained by synthesizing compounds (II) through a compound (I) as an intermediate. According to the present invention, the intended compound (I) is obtained by reacting 6-methyl-2,3,4-trimethoxyphenol (III) with iso (prenol) (IV) of the general formula:

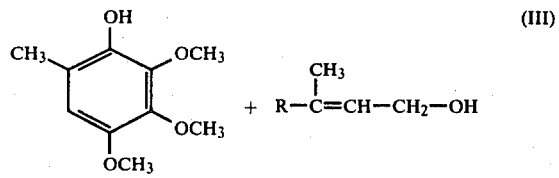

or an iso-derivative thereof of the formula:

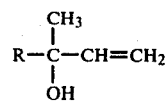

wherein R has the same meaning as above in the presence of a complex catalyst comprising a Lewis acid and a silica-alumina compound. As (iso) prenols (IV) used in the present invention, there may be mentioned, for example, 3-methylbutene-2-ol-1, 3-methylbutene-1-ol-3, geraniol, linalool, nerol, nerolidol, phytol, isophytol, geranylgeraniol, geranyllinalool, geranylfarnesol, geranylnerolidol, farnesylfarnesol, farnesylnerolidol, geranylgeranylfarnesol, solanesol, decaprenol and isodecaprenol.

As the silica alumina compound which is one of components of the complex catalyst, there may be mentioned, for example, china clay, activated clay, kaolin, natural and synthetic zeolite, silica alumina, silica alumina boria and silica alumina magnesia. As the Lewis acid which is another component of the complex catalyst, there may be mentioned, for example, boron trifluoride and ether complexes thereof, zinc chloride, aluminum chloride and tin chloride. The complex catalyst can be used in a suitable manner, for example, by adding the two components of the catalyst separately to join them together by mixing or the like at the site of the reaction or by previously adsorbing a Lewis acid, which is one of the components, on silica alumina compound, which is the other component, and the reaction is carried out in the presence of the adsorption product.

In carrying out the reaction, it is preferred to use a solvent selected suitably, for example, an aromatic hydrocarbon solvent such as benzene, toluene or xylene; an ether solvent such as ethyl ether, isopropyl ether or tetrahydrofuran; an aliphatic hydrocarbon solvent such as pentane, hexane, heptane, octane, isooctane, petroleum ether or ligroin; or an ester solvent such as ethyl acetate.

The reaction proceeds at a relatively low temperature of 0°–50° C., preferably around 40° C. and, therefore, a fear of causing side reactions due to heating is scarce. Compound (I) thus obtained can be converted easily to compound (II) according to a conventional process for quinone formation by oxidizing the phenol compound with a mild oxidizing agent such as silver oxide, lead dioxide, ferric chloride or aqueous hydrogen peroxide solution. In this case, crude compound (I) can be transferred directly into the oxidation step without purification treatment.

By employing the process of the present invention and the compound (I) as an intermediate in the synthesis of the compound (II) which is important from medical and pharmaceutical viewpoints, the following significant improvements were obtained over the above described conventional processes:

(i) Reduction in number of steps:

In the preparation of the compound (II) from the compound (III) according to conventional processes, the number of steps is not small (4–5 steps) which include converting compound (III) into 2,3-dimethoxy-5-methyl-1,4-benzoquinone by, for example, a method of Japanese Patent Publication No. 28503/1974, reducing the same into 2,3-dimethoxy-5-methyl-1,4-benzohydroquinone, monoacylating the same, if necessary, then condensing the same with (iso) prenol or a reactive derivative thereof to form 2,3-dimethoxy-5-prenyl-6-methyl-1,4-benzohydroquinone or monoacylate thereof (see Japanese Patent Publication No. 17513/1964) and oxidizing the same to obtain the intended product (II) (see Japanese Patent Publication No. 17514/1964) and which processes involve troublesome operations. On the other hand, the compound (II) can be obtained from the compound (III) in only two steps according to the process of the present invention by using the compound (I) of the invention as intermediate and each step comprises a simple operation.

(ii) Improvement in yield:

According to the process of the present invention, the yield of the compound (I) from the compound (III) is as high as 70–80% (purified product) and conversion of the compound (I) into compound (II) proceeds substantially stoichiometrically in a yield of 90–95%. Consequently, as a whole, the compound (II) can be obtained from the compound (III) in a very high yield. For example, in case of Co $Q_{10}$, the pure product was obtained in a yield of 70% or higher.

(iii) Effects of preventing corrosion of device, etc., and preventing environmental pollution:

Lewis acids such as zinc chloride, boron trifluoride and ether complexes thereof have generally a property of corroding the reaction device strongly and, therefore, the use of anticorrosive reaction device is inevitable. However, this demerit can be overcome by adsorbing those Lewis acids on a silica alumina compound. Further, environmental pollution can be prevented, since metal ion elution is not caused.

Therefore, the process of the present invention can be considered to be industrially more excellent than the conventional processes.

The following examples illustrate the present invention.

EXAMPLE 1

Synthesis of 2-methyl-3-decaprenyl-4,5,6-trimethoxyphenol

38 Grams of 2,3,4-trimethoxy-6-methylphenol were dissolved in 30 ml. of n-hexane. The solution was added with 30 g of silica alumina N 633HN (a product of Nikki Kagaku) and then added dropwise with 10 g of boron trifluoride ether complex over 15 minutes under stirring while the temperature was kept at 40° C. Then, a solution of 26 g of decaprenol (purity 75%) in 15 ml. of n-hexane was added thereto dropwise over 40 minutes under stirring at the same temperature. Stirring was continued for an additional 10 minutes at the same temperature. After completion of the reaction, the reaction mixture was subjected to filtration. The filtrate was washed with methanolic aqueous sodium hydroxide solution (mixture of 10% aqueous sodium hydroxide solution and methanol in a ratio of 1:2) and then with aqueous methanol solution (mixture of water and methanol in a ratio of 1:2) till the liquor became neutral. The aqueous layer was separated out and the solvent layer was concentrated under reduced pressure to obtain 30 g of light yellow oily product. The product was purified by silica gel chromatography (elution solvent: mixture of n-hexane/isopropyl ether) to obtain white crystals.

Yield: 19.0 g (77.5%)
Melting point: 43.5°–44° C.
Elementary analysis as $C_{60}H_{94}O_4$:
Theoretical (%): C 81.95, H 10.77
Found (%): C 81.76, H 10.80

EXAMPLE 2

Synthesis of 2-methyl-3-decaprenyl-4,5,6-trimethoxyphenol

38 Grams of 2,3,4-trimethoxy-6-methylphenol were dissolved in 35 ml. of benzene. The solution was added with 35 g of the same silica alumina N 633HN as in Example 1 and 10 g of aluminum chloride and then the whole was stirred for 30 minutes while the temperature was kept at 40° C. Then, a solution of 26 g of decaprenol (purity 75%) in 15 ml. of benzene was added thereto dropwise over 40 minutes at 35° C. Stirring was continued for an additional 10 minutes at the same temperature. After completion of the reaction, the reaction mixture was subjected to filtration. The filtrate was treated in the same manner as in Example 1 and the solvent layer was concentrated under reduced pressure to obtain 32 g of light yellow oily product. A part of the product was purified by silica gel chromatography (elution solvent: mixture of hexane/isopropyl ether) to obtain white crystals of a melting point of 43.3°–44° C.

Elementary analysis as $C_{60}H_{94}O_4$:
Theoretical (%): C 81.95, H 10.77
Found (%): C 81.80, H 10.75

REFERENTIAL EXAMPLE

Synthesis of 2,3-dimethoxy-5-decaprenyl-6-methylbenzoquinone (CO $Q_{10}$):

17.3 Grams of 2-methyl-3-decaprenyl-4,5,6-trimethoxyphenol were dissolved in a solvent comprising a mixture of 35 ml. of ethyl acetate and 100 ml. of isopropyl ether. The solution was added with 50 g of ferric chloride hexahydrate and the whole was stirred at room temperature for 30 minutes. Then, the whole was washed with 150 ml. of water three times. The organic solvent layer was separated out and the solvent was distilled under reduced pressure. The resulting light reddish brown oily product was purified by silica gel chromatography (elution solvent: mixture of n-hexane/isopropyl ether) to obtain light yellowish orange oily product.

Yield 16.1 g (93%)

A part of the product was taken and crystallized from acetone to obtain a sample for identification.

Light yellow amorphous crystals m.p. 49°–50° C.

Results of elementary analysis, U.V., I.R., NMR and MAS spectrum data coincided with those of the standard.

The embodiments of the invention in which an exclusive property or privilege is claimed are defined as follows:

1. A process for synthesizing 2-methyl-3-decaprenyl-4,5,6-trimethoxyphenol, which comprises reacting 6-methyl-2,3,4-trimethoxyphenol with decaprenol, in a solvent, at a temperature of from 0° to 50° C., in the presence of a complex catalyst comprising boron trifluoride ether complex mixed with silica alumina.

2. A process for synthesizing 2-methyl-3-decaprenyl-4,5,6-trimethoxyphenol, which comprises reacting 6-methyl-2,3,4-trimethoxyphenol with decaprenol, in a solvent, at a temperature of from 0° to 50° C., in the presence of a complex catalyst comprising aluminum chloride mixed with silica alumina.

* * * * *